United States Patent [19]
Foster et al.

[11] Patent Number: 5,641,655
[45] Date of Patent: Jun. 24, 1997

[54] METHODS FOR PRODUCING THROMBOPOIETIN POLYPEPTIDES USING A MAMMALIAN TISSUE PLASMINOGEN ACTIVATOR SECRETORY PEPTIDE

[75] Inventors: Donald C. Foster; Mark D. Heipel; Richard D. Holly, all of Seattle, Wash.

[73] Assignee: ZymoGenetics, Inc., Seattle, Wash.

[21] Appl. No.: 347,029

[22] Filed: Nov. 30, 1994

[51] Int. Cl.$^6$ .............. C12N 15/19; C12N 15/62; C07H 21/04

[52] U.S. Cl. .............. 435/69.7; 435/69.5; 435/69.8; 435/172.3; 435/254.2; 435/254.21; 435/254.23; 435/325; 435/419; 435/348; 435/349; 435/352; 435/359; 536/23.4; 935/10; 424/85.1

[58] Field of Search .............. 536/23.5, 23.4; 530/351; 435/69.7, 69.8, 69.5, 172.3, 240.2, 252.3, 320.1, 254.2, 254.21, 254.23; 424/85.1

[56] References Cited

U.S. PATENT DOCUMENTS

| | | | |
|---|---|---|---|
| 5,037,743 | 8/1991 | Welch et al. | 435/69.1 |
| 5,171,844 | 12/1992 | van Ooyen et al. | 530/383 |
| 5,284,755 | 2/1994 | Gearing et al. | 435/69.1 |

FOREIGN PATENT DOCUMENTS 486193  5/1992  European Pat. Off. .

OTHER PUBLICATIONS

D.T. Berg et al. Biochem. Biophys. Res. Commun. 179(3):1289–1296, Sep. 30, 1991.
Sohma et al., *FEBS Letters* 353:57–61 1994.
Krasney et al., Cytokine 4(2):134–143, Mar. 1992.
J.M. Cregg et al., Bio/Technology 11:905–910, Aug. 1993.
de Sauvage et al., *Nature* 369: 533–538, 1994.
Bartley et al., *Cell* 77: 1117–1124, 1994.
Lok et al., *Nature* 369: 565–568, 1994.
Pennica et al., *Nature* 301: 214–221, 1983.
U.S. Patent Application Serial No. 08/196,025 filed Feb. 14, 1994.
U.S. Patent Application Serial No. 08/203,197 filed Feb. 25; 1994.
U.S. Patent Application Serial No. 08/215,203 filed Mar. 21, 1994.
U.S. Patent Application Serial No. 08/252,491 filed Jun. 1, 1994.
U.S. Patent Application Serial No. 07/998,972, fild Dec. 20, 1992.

*Primary Examiner*—Stephen Walsh
*Assistant Examiner*—L. Spector
*Attorney, Agent, or Firm*—Gary E. Parker; Debra K. Leith; Deborah A. Sawislak

[57] ABSTRACT

DNA constructs useful in the production of thrombopoietin are disclosed. In general, the DNA constructs comprise a first DNA segment encoding a fusion of an amino-terminal secretory peptide joined to a thrombopoietin polypeptide and one or more additional DNA segments that provide for the transcription of the first segment. The secretory peptide is a native mammalian t-PA secretory peptide or may be modified to enhance proteolytic cleavage of the fusion. Also disclosed are cultured eukaryotic cells containing these DNA constructs and methods for producing thrombopoietin polypeptides through the use of the DNA constructs and cultured eukaryotic cells.

26 Claims, No Drawings

METHODS FOR PRODUCING THROMBOPOIETIN POLYPEPTIDES USING A MAMMALIAN TISSUE PLASMINOGEN ACTIVATOR SECRETORY PEPTIDE

BACKGROUND OF THE INVENTION

Hematopoiesis is the process by which blood cells develop and differentiate from pluripotent stem cells in the bone marrow. This process involves a complex interplay of polypeptide growth factors (cytokines) acting via membrane-bound receptors on the target cells. Cytokine action results in cellular proliferation and differentiation, with a response to a particular cytokine often being lineage-specific and/or stage-specific. Development of a single cell type, such as a platelet, from a stem cell may require the coordinated action of a plurality of cytokines acting in the proper sequence.

The known cytokines include the interleukins, such as IL-1, IL-2, IL-3, IL-6, IL-8, etc.; and the colony stimulating factors, such as G-CSF, M-CSF, GM-CSF, erythropoietin (EPO), etc. In general, the interleukins act as mediators of immune and inflammatory responses. The colony stimulating factors stimulate the proliferation of marrow-derived cells, activate mature leukocytes, and otherwise form an integral part of the host's response to inflammatory, infectious, and immunologic challenges.

Various cytokines have been developed as therapeutic agents. For example, erythropoietin, which stimulates the development of erythrocytes, is used in the treatment of anemia arising from renal failure. Several of the colony stimulating factors have been used in conjunction with cancer chemotherapy to speed the recovery of patients' immune systems. Interleukin-2, α-interferon and γ-interferon are used in the treatment of certain cancers. An activity that stimulates megakaryocytopoiesis and thrombocytopoiesis has been identified in body fluids of thrombocytopenic animals and is referred to in the literature as "thrombopoietin" (recently reviewed by McDonald, *Exp. Hematol.* 16:201–205, 1988 and McDonald, *Am. J. Ped. Hematol. Oncol.* 14:8–21, 1992).

Recently, several groups have identified and/or cloned a protein that binds to the cellular mpl receptor and stimulates megakaryocytopoiesis and thrombocytopoiesis. See, de Sauvage et al., *Nature* 369:533–538, 1994; Lok et al., *Nature* 369:565–568, 1994; Kaushansky et al., *Nature* 369:568–571, 1994; Wendling et al., *Nature* 369:571–574, 1994; and Bartley et al., *Cell* 77:1117–1124, 1994. It has been proposed that this protein be termed thrombopoietin (Kaushansky et al., ibid.).

Analysis of amino acid sequences indicates that the mature mouse TPO extends from amino acid residue 45 (Ser) to residue 379 (Thr) of SEQ ID NO: 2. The predicted amino terminus of the human protein corresponds precisely to the demonstrated mature amino terminus for recombinant murine TPO (Lok et al., ibid.), i.e. it is at Ser (22) of SEQ ID NO:4, with the protein extending to amino acid residue 353 of SEQ ID NO:4. TPO is subject to proteolysis and has been isolated in heterogeneous or degraded form (de Sauvage et al., *Nature* 369:533–538, 1994; Bartley et al., *Cell* 77:1117–1124, 1994). Molecular species as small as 25 kD have been found to be active in vitro (Bartley et al., ibid.), and recombinant human TPO polypeptides of 153 (de Sauvage et al., ibid) and 174 amino acids (Bartley et al., ibid) have been reported as being active in vitro, as has the product of expression of the full-length human cDNA, which encodes a primary translation product of 353 amino acids (Bartley et al., ibid).

Thrombopoietin appears to be subject to proteolysis and was isolated in heterogeneous or degraded form (Bartley et al., ibid.; de Sauvage et al., ibid.). Preparations of thrombopoietin reported in the scientific literature are therefore not well characterized as to composition and the relative activities of the various molecular species, although at least some of the proteolytic products are biologically active. However, little work has been done to date on the large-scale production of thrombopoietin, and there remains a need in the art for methods of producing the protein in large amounts and in a cost-effective manner.

SUMMARY OF THE INVENTION

It is an object of the present invention to provide methods for the production of thrombopoietin.

It is a further object of the present invention to provide methods for directing the secretion of recombinant thrombopoietin from host cells.

It is yet a further object of the invention to provide DNA constructs that direct the expression and secretion of high levels of thrombopoietin.

Within one aspect of the present invention there is provided a DNA construct comprising (a) a first DNA segment encoding a polypeptide fusion, the fusion comprising an amino-terminal secretory peptide joined to a thrombopoietin (TPO) polypeptide, the joined peptide and polypeptide defining a proteolytic cleavage site at their junction; and (b) one or more additional DNA segments operably linked to the first DNA segment so as to provide for its transcription, wherein the secretory peptide is selected from the group consisting of native mammalian tissue plasminogen activator (t-PA) secretory peptides and mammalian t-PA secretory peptides modified to enhance proteolytic cleavage at the junction. Within one embodiment, the secretory peptide is a human t-PA secretory peptide. Within a related embodiment, the secretory peptide consists of a sequence of amino acid residues as shown in SEQ ID NO:5 wherein Xaa(29), Xaa(31) and Xaa(33) are individually any amino acid and Xaa(34) is Ala, Arg or Lys. Within another embodiment, Xaa(29) and Xaa(31) are individually any amino acid except Lys, Arg or His. Within additional embodiments, Xaa(33) is Gly; Xaa(34) is Arg or Lys; Xaa(29) and Xaa(31) are individually Asp, Glu, Gln, Gly or Ala, Xaa(33) is Gly, and Xaa(34) is Arg; or Xaa(29) is Arg or Glu, Xaa(31) is Arg or Gln, Xaa(33) is Gly, and Xaa(34) is Arg, subject to the limitation that at least one of Xaa(29) and Xaa(31) is not Arg. Within another embodiment, the TPO polypeptide consists of from 144 to 335 amino acid residues. Within a related embodiment, the TPO polypeptide consists of from 144 to 191 amino acid residues. Within another embodiment, the TPO polypeptide consists of a sequence of amino acids selected from the group consisting of a sequence as shown in SEQ ID NO:4 from Ser(22) to Val(173), Ser(22) to Arg(185), Set(22) to Asn(193), Set(22) to Phe(207), or Set(22) to Gin(235).

Within another aspect of the invention there is provided a DNA construct comprising a first DNA segment encoding a polypeptide fusion consisting essentially of an amino-terminal secretory peptide as shown in SEQ ID NO:5 wherein Xaa(29) is Arg or Glu, Xaa(31) is Arg or Gln, Xaa(33) is Gly, and Xaa(34) is Ala or Arg, joined to a TPO polypeptide of from 144 to 335 amino acids, wherein the first DNA segment is operably linked to one or more additional DNA segments that provide for its transcription. Within one embodiment, the TPO polypeptide consists of from 144 to 191 amino acid residues. Within another embodiment, the TPO polypeptide is a human TPO polypeptide. Within another embodiment, the TPO polypeptide consists of a sequence of amino acids selected from the group consisting of a sequence as shown in SEQ ID NO:4 from Ser(22) to Val(173), Ser(22) to Arg(185), Ser(22) to Asn(193), Ser(22) to Phe(207), or Ser(22) to Gln(235). Within another embodiment, the DNA construct further comprises a selectable marker.

Within a third aspect, the present invention provides a cultured eukaryotic cell containing a DNA construct as disclosed above. Within one group of embodiments, the cell is a yeast cell, such as a *Saccharomyces cerevisiae* cell or a *Pichia pastoris* cell. Within another group of embodiments, the cell is a mammalian cell, such as a rodent cell or a kidney cell.

Within a fourth aspect of the invention there is provided a method for producing a thrombopoietin polypeptide comprising the steps of culturing a eukaryotic cell as disclosed above wherein the cell expresses the first DNA segment and the TPO polypeptide is secreted from the cell, and the TPO polypeptide is selectively recovered.

These and other aspects of the invention will become evident upon reference to the following detailed description.

DETAILED DESCRIPTION OF THE INVENTION

Prior to describing the present invention in detail, it may be helpful to define certain terms used herein:

Allelic variant: An alternative form of a gene that arises through mutation, or an altered polypeptide encoded by the mutated gene. Gene mutations can be silent (no change in the encoded polypeptide) or may encode polypeptides having altered amino acid sequence.

cDNA: Complementary DNA, prepared by reverse transcription of a messenger RNA template, or a clone or amplified copy of such a molecule. Complementary DNA can be single-stranded or double-stranded.

Expression vector: A DNA molecule, linear or circular, that comprises a segment encoding a polypeptide of interest operably linked to additional segments that provide for its transcription. Such additional segments include promoter and terminator sequences. An expression vector may also include one or more origins of replication, one or more selectable markers, an enhancer, a polyadenylation signal, etc. Expression vectors are generally derived from plasmid or viral DNA, or may contain elements of both. The term "operably linked" indicates that the segments are arranged so that they function in concert for their intended purposes, e.g. transcription initiates in the promoter and proceeds through the coding segment to the terminator.

Gene: A segment of chromosomal DNA that encodes a polypeptide chain. A gene includes one or more regions encoding amino acids, which in some cases are interspersed with non-coding "intervening sequences" ("introns"), together with flanking, non-coding regions which provide for transcription of the coding sequence.

Signal Sequence: A DNA sequence encoding a secretory peptide. Signal sequences are also called leader sequences, prepro sequences and pre sequences. A secretory peptide is an amino acid sequence that acts to direct the secretion of a mature polypeptide or protein from a cell. Secretory peptides are characterized by a core of hydrophobic amino acids and are typically (but not exclusively) found at the amino termini of newly synthesized proteins. Very often the secretory peptide is cleaved from the mature protein during secretion in one or more cleavage events. Such secretory peptides contain processing sites that allow cleavage of the secretory peptides from the mature proteins as they pass through the secretory pathway. The term "amino-terminal secretory peptide" is used herein to denote a secretory peptide that occurs at the amino terminus of a protein (including fusion proteins).

Promoter: The portion of a gene at which RNA polymerase binds and mRNA synthesis is initiated.

Thrombopoietin: Thrombopoietin (TPO) proteins are characterized by their ability to specifically bind to MPL receptor from the same species and to stimulate platelet production in vivo. In normal test animals, TPO is able to increase platelet levels by 100% or more within 10 days after beginning daily administration. The term "thrombopoietin polypeptide" encompasses full-length thrombopoietin molecules and biologically active portions thereof, that is fragments of a thrombopoietin that exhibit the qualitative biological activities of the intact molecule (receptor binding and in vivo stimulation of platelet production).

Amino acids are represented herein by the standard three-letter codes, with variable amino acids represented by "Xaa". Amino acid positions are designated by numbers in parentheses following the three-letter amino acid designations. For example, Ser(22) indicates a serine residue at position 22 of an amino acid sequence, and Xaa(29) indicates a variable amino acid at position 29 of a sequence. When a sequence contains a plurality of variable amino acids, each is represented by Xaa, although each may be a different amino acid residue.

The present invention provides methods for producing recombinant TPO polypeptides that are secreted from host cells expressing them, as well as DNA constructs, cells, and other materials that are useful within these methods.

Representative mouse and human TPO DNA and amino acid sequences are shown in SEQ ID NOS: 1, 2, 3 and 4. Those skilled in the art will recognize that the disclosed sequences represent single alleles, and that allelic variation is expected to exist. Allelic variants of the disclosed sequences are within the scope of the present invention.

The mouse and human TPO sequences disclosed herein can be used to design strategies and tools to clone additional TPO-encoding polynucleotides. The present invention thus provides methods for preparing TPO polypeptides from a variety of species. Mammalian TPO polypeptides are preferred, including human, mouse, rat, porcine, canine, ovine, bovine and equine TPO polypeptides. Of particular interest are primate TPO polypeptides, in particular human TPO polypeptides.

Thrombopoietin polypeptides that can be produced according to the present invention include full-length thrombopoietin molecules, as well as truncated, biologically active fragments of the mature protein. In general these TPO polypeptides include at least the core "EPO-like domain" (so named because of its homology to erythropoietin) of the N-terminal region of the molecule. This core EPO-like domain is bounded by cysteine residues at positions 51 and 195 of mouse TPO (SEQ ID NO:2); positions 28 and 172 of human TPO (SEQ ID NO:4); and their counterpart residues in TPOs of other species. It has now been found that TPO polypeptides, such as a mouse TPO polypeptide extending from amino acid residue 45 (Ser) to residue 216 (Asn) of SEQ ID NO:2, are active in promoting platelet production in experimental animals. Particularly preferred TPO polypeptides are shown below in Table 1.

TABLE 1

Mouse TPO (SEQ ID NO:2)

Cys (residue 51)—Cys (residue 195)
Cys (51)—Val (196)
Cys (51)—Pro (206)
Cys (51)—Ser (207)
Cys (51)—Asn (216)
Cys (51)—Arg (235)
Cys (51)—Arg (244)
Cys (51)—Arg (249)
Cys (51)—Gln (259)
Cys (51)—Arg (273)
Ser (45)—Cys (195)
Ser (45)—Val (196)
Ser (45)—Pro (206)
Ser (45)—Ser (207)
Ser (45)—Asn (216)
Ser (45)—Arg (235)
Ser (45)—Arg (244)
Ser (45)—Arg (249)
Ser (45)—Gln (259)
Ser (45)—Arg (273)

Human TPO (SEQ ID NO:4)

Cys (28)—Cys (172)
Cys (28)—Val (173)
Cys (28)—Arg (175)
Cys (28)—Arg (185)
Cys (28)—Asn (193)
Cys (28)—Arg (198)
Cys (28)—Phe (207)
Cys (28)—Gln (235)
Cys (28)—Arg (266)
Ser (22)—Cys (172)
Ser (22)—Val (173)
Ser (22)—Arg (175)
Ser (22)—Arg (185)
Ser (22)—Asn (193)
Ser (22)—Arg (198)
Ser (22)—Phe (207)
Ser (22)—Gln (235)
Ser (22)—Arg (266)

Those skilled in the art will recognize that molecules having termini between the preferred amino- and carboxyl-terminal residues disclosed in Table 1 can be produced and would be expected to be biologically active.

Thrombopoietin polypeptides may include one or more amino acid substitutions, deletions or additions, either from natural mutation or human manipulation of DNA. These changes are preferably of a minor nature, such as conservative amino acid substitutions that do not significantly affect the folding or activity of the protein (see Table 2). See, in general Ford et al., *Protein Expression and Purification* 2: 95–107, 1991, which is incorporated herein by reference.

TABLE 2

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |

TABLE 2-continued

Conservative amino acid substitutions

| | |
|---|---|
| Small: | glycine |
| | alanine |
| | serine |
| | threonine |
| | methionine |

Essential amino acids in TPO can be identified according to procedures known in the art, such as site-directed mutagenesis or alanine-scanning mutagenesis (Cunningham and Wells, *Science* 244, 1081–1085, 1989). In the latter technique, single alanine mutations are introduced at every residue in the molecule, and the resultant mutant molecules are tested for biological activity (e.g. receptor binding, in vitro or in vivo proliferative activity) to identify amino acid residues that are critical to the activity of the molecule. Sites of ligand-receptor interaction can also be determined by analysis of crystal structure as determined by such techniques as nuclear magnetic resonance, crystallography or photoaffinity labeling. See, for example, de Vos et al., *Science* 255:306–312, 1992; Smith et al., *J. Mol. Biol.* 224:899–904, 1992; Wlodaver et al., *FEBS Lett.* 309:59–64, 1992.

In general, cytokines are predicted to have a four-alpha helix structure, with the first and fourth helices being most important in ligand-receptor interactions and more highly conserved among members of the family. Referring to the human TPO amino acid sequence shown in SEQ ID NO:4, alignment of cytokine sequences suggests that these helices are bounded by amino acid residues 29 and 53, 80 and 99, 108 and 130, and 144 and 168, respectively (boundaries are ±4 residues). Helix boundaries of the mouse (SEQ ID NO:2) and other non-human TPOs can be determined by alignment with the human sequence. Other important structural aspects of TPO include the cysteine residues at positions 51, 73, 129 and 195 of SEQ ID NO:2 (corresponding to positions 28, 50, 106 and 172 of SEQ ID NO:4).

TPO polypeptides produced according to the present invention are characterized as having 50%, preferably 60%, more preferably at least 80%, sequence identity to the corresponding portion of the sequence shown in SEQ ID NO: 2, the sequence shown in SEQ ID NO:4, or their species homologs. Such polypeptides will more preferably be at least 90% identical, and most preferably 95% or more identical to SEQ ID NO: 2 or SEQ ID NO:4 or their species homologs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

TPO polypeptides may further include one or more additional, non-TPO, amino acid residues up to a total of about 20–25 residues, typically as an amino- or carboxyl-terminal extension of a polypeptide. Extensions of this type include, for example, an amino-terminal methionine residue, small linker peptides, and peptide extensions that facilitate purification of the polypeptide, such as a polyhistidine tract, an antigenic epitope, or a binding domain. See, in general, Ford et al., Protein Expression and Purification 2:95–107, 1991, which is incorporated herein by reference.

As noted above, TPO appears to be sensitive to proteolysis, and proteolytic products of the full-length (as inferred from cDNA sequence) molecule have been shown to be active. However, attempts in the inventors' laboratory to produce mouse TPO met with only limited success due to inefficient secretion of the polypeptide. The inventors discovered that by substituting a synthesized secretory peptide derived from that of human tissue-type plasminogen activator (t-PA), shown in SEQ ID NO:5, for the native TPO signal peptide, production of recoverable TPO in cultured baby hamster kidney (BHK) cells was increased by a factor of five to ten.

Within the present invention, a t-PA secretory peptide or derivative thereof is used to direct the secretion of TPO. In general, a DNA segment encoding a secretory peptide-TPO polypeptide fusion is operably linked to one or more additional DNA segments that provide for its transcription. Such additional DNA segments include a transcription promoter. It is preferred to also link the DNA sequence encoding a secretory peptide-TPO fusion to a transcription terminator, although transcription will in many cases terminate fortuitously within vector sequences downstream of the fusion sequence. The vector will commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a TPO polypeptide into the secretory pathway of the host cell, a DNA sequence encoding a secretory peptide is joined to a DNA sequence encoding a TPO polypeptide in the correct reading frame so that the joined sequences encode a fusion protein. The joined secretory peptide and TPO polypeptide define a proteolytic cleavage site at their junction. In general, the present invention makes use of a secretory peptide having the sequence Met-Asp-Ala-Met-Lys-Arg-Gly-Leu-Cys-Cys-Val-Leu -Leu-Leu-Cys-Gly-Ala-Val-Phe-Val-Ser-Pro-Ser-Gln-Glu-Ile -His-Ala-Xaa-Phe-Xaa-Arg-Xaa-Xaa-Arg (SEQ ID NO:5) wherein Xaa (29), Xaa(31) and Xaa(33) are individually any amino acid and Xaa(34) is Ala, Arg or Lys. While the wild-type secretory peptide of human t-PA (wherein Xaa(29) and Xaa(31) are Arg, Xaa(33) is Gly and Xaa(34) is Ala) may be employed, it contains a pair of arginine residues at positions -4 and -5 (residues 31 and 32 of SEQ ID NO:5), which provide a proteolytic processing site. Cleavage can occur at this site, resulting in the production of a TPO polypeptide having three additional N-terminal amino acids. It is therefore preferred within the present invention to modify the DNA sequence encoding the secretory peptide to eliminate this processing site and to enhance processing at the junction of the t-PA and TPO sequences. While not wishing to be bound by theory, it is believed that secretory peptide cleavage is dependent upon a prohormone converting enzyme, such as the yeast KEX2 gene product or the mammalian enzymes PC1, PC2 and furin. Enzymes of this type recognize cleavage sites characterized by arginine residues in the -1 and -4 positions. Cleavage is facilitated by a basic amino acid residue (e.g. Lys or Arg) in the -2 position. Within the present invention cleavage between the secretory peptide and TPO polypeptide may therefore be enhanced by providing arginine residues at the -1 and -4 positions, and optionally by providing a basic amino acid residue at the -2 position. Additional enhancement of the desired cleavage is achieved by replacing arginine residues elsewhere in the secretory peptide with other, preferably non-basic, amino acid residues, in particular where such residues form an Arg-Xaa-Xaa-Arg motif. Within a preferred embodiment, Xaa(29) and Xaa(31) in SEQ ID NO:5 are individually any amino acid except Lys, Arg or His. More preferably, Xaa(29) and Xaa(31) are individually Asp, Glu, Gln, Gly or Ala. Within another preferred embodiment, Xaa(33) is Gly. Within another preferred embodiment, Xaa(34) is Arg or Lys. Particularly preferred substitutions include Glu at Xaa (29), Gln at Xaa(31), and Arg at Xaa(34). Signal sequences are mutagenized by conventional methods, such as the polymerase chain reaction disclosed by Mullis et al., U.S. Pat. No. 4,683,195 and Mullis, U.S. Pat. No. 4,683,202, which are incorporated herein by reference in their entirety.

Secretory peptides from non-human t-PAs, and derivatives of non-human t-PA secretory peptides, may also be used. The DNA sequences encoding t-PA secretory peptides from various species are known in the art and have been disclosed by, for example, Rickles et al., J. Biol. Chem. 263.:1563–1560, 1988 and Feng et al., J. Biol. Chem. 265:2022–2027, 1990. Such DNA sequences can be cloned as cDNA or genomic molecules according to techniques that are standard in the art, or can be synthesized, preferably using automated equipment and the application of conventional synthetic protocols.

Suitable host cells for use within the present invention include any type of cell that can be engineered to express heterologous DNA, can be grown in culture, and has a secretory pathway. Although prokaryotic cells, such as E. coli cells, are capable of secreting proteins at least into the periplasmic space, it is preferred within the present invention to use cultured eukaryotic cells, such as fungal cells or, in particular, cultured mammalian cells.

Yeast cells, particularly cells of the genus Saccharomyces, are useful in producing recombinant TPO polypeptides. Yeast cells have a long history of use in the production of products for human consumption and are relatively inexpensive to culture. Methods for transforming yeast cells with exogenous DNA and producing recombinant proteins therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075, which are incorporated herein by reference. Transformed cells are selected by phenotype determined by a selectable marker, commonly drug resistance or the ability to grow in the absence of a particular nutrient (e.g. leucine). A preferred vector system for use in yeast is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092, which are incorporated herein by reference) and alcohol dehydrogenase genes. See also U.S. Pat. Nos. 4,990,446; 5,063,154; 5,139,936 and 4,661,454, which are incorporated herein by reference. Transformation systems for other yeasts, including Hansenula polymorpha, Schizosaccharomyces pombe, Kluyveromyces lactis, Kluyveromyces fragilis, Ustilago maydis, Pichia pastoris, Pichia guillermondii and Candida maltosa are known in the art. See, for example, Gleeson et al., J. Gen. Microbiol. 132:3459–3465, 1986; Cregg, U.S. Pat. No. 4,882,279; and Stroman et al., U.S. Pat. No. 4,879,231.

Other fungal cells are also suitable as host cells. For example, Aspergillus cells may be utilized according to the methods of McKnight et al., U.S. Pat. No. 4,935,349, which is incorporated herein by reference. Methods for transforming Acremonium chrysogenum are disclosed by Sumino et al., U.S. Pat. No. 5,162,228, which is incorporated herein by reference. Methods for transforming Neurospora are disclosed by Lambowitz, U.S. Pat. No. 4,486,533, which is incorporated herein by reference.

As noted above, cultured mammalian cells are preferred hosts within the present invention. Methods for introducing exogenous DNA into mammalian host cells include calcium phosphate-mediated transfection (Wigler et al., Cell 14:725, 1978; Corsaro and Pearson, Somatic Cell Genetics 7:603, 1981: Graham and Van der Eb, Virology 52:456, 1973), electroporation (Neumann et al., EMBO J.. 1:841–845, 1982), DEAE-dextran mediated transfection (Ausubel et al., eds., Current protocols in Molecular Biology, John Wiley and Sons, Inc., New York, 1987), and cationic lipid-mediated transfection (Hawley-Nelson et al., Focus 15:73–79, 1993), which are incorporated herein by reference. The production of recombinant proteins in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., J. Gen. Virol. 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978, which are incorporated herein by reference) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. Transformation of insect cells and production of foreign proteins therein is disclosed by Guarino et al., U.S. Pat. No. 5,162, 222; Bang et al., U.S. Pat. No. 4,775,624; and WIPO publication WO 94/06463, which are incorporated herein by reference. The use of Agrobacterium rhizogenes as a vector for expressing genes in plant cells has been reviewed by Sinkar et al., J. Biosci. (Bangalore) 11:47–58, 1987.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

TPO prepared according to the present invention is selectively recovered using methods generally known in the art, such as affinity purification and separations based on size, charge, solubility and other properties of the protein. When the protein is produced in cultured mammalian cells, it is preferred to culture the cells in a serum-free culture medium in order to limit the amount of contaminating protein. The medium is harvested and fractionated. Preferred methods of fractionation include affinity chromatography, such as on an immobilized MPL receptor protein or ligand-binding portion thereof or through the use of an affinity tag (e.g. polyhistidine, substance P or other polypeptide or protein for which an antibody or other specific binding agent is available). A specific cleavage site may be provided between the protein of interest and the affinity tag. Other chromatographic methods can also be employed, such as cation exchange chromatography, anion exchange chromatography, and hydrophobic interaction chromatography.

TPO prepared according to the present invention can be used therapeutically wherever it is desirable to increase proliferation of cells in the bone marrow, such as in the treatment of cytopenia, such as that induced by aplastic anemia, myelodisplastic syndromes, chemotherapy or congenital cytopenias. TPO is also useful for increasing platelet production, such as in the treatment of thrombocytopenia. Thrombocytopenia is associated with a diverse group of diseases and clinical situations that may act alone or in concert to produce the condition. Lowered platelet counts can result from, for example, defects in platelet production, abnormal platelet distribution, dilutional losses due to massive transfusions, or abnormal destruction of platelets. For example, chemotherapeutic drugs used in cancer therapy may suppress development of platelet progenitor cells in the bone marrow, and the resulting thrombocytopenia limits the chemotherapy and may necessitate transfusions. In addition, certain malignancies can impair platelet production and platelet distribution. Radiation therapy used to kill malignant cells also kills platelet progenitor cells. Thrombocytopenia may also arise from various platelet autoimmune disorders induced by drugs, neonatal alloimmunity or platelet transfusion alloimmunity. TPO can reduce or eliminate the need for transfusions, thereby reducing the incidence of platelet alloimmunity. Abnormal destruction of platelets can result from: (1) increased platelet consumption in vascular grafts or traumatized tissue; or (2) immune mechanisms associated with, for example, drug-induced thrombocytopenia, idiopathic thrombocytopenic purpura (ITP), autoimmune diseases, hematologic disorders such as leukemia and lymphoma or metastatic cancers involving bone marrow. Other indications for TPO include aplastic anemia and drug-induced marrow suppression resulting from, for example, chemotherapy or treatment of HIV infection with AZT.

Thrombocytopenia is manifested as increased bleeding, such as mucosal bleedings from the nasal-oral area or the gastrointestinal tract, as well as oozing from wounds, ulcers or injection sites.

For pharmaceutical use, TPO is formulated for parenteral, particularly intravenous or subcutaneous, delivery according to conventional methods. Intravenous administration will be by bolus injection or infusion over a typical period of one to several hours. In general, pharmaceutical formulations will include TPO in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. In addition, TPO may be combined with other cytokines, particularly early-acting cytokines such as stem cell factor, IL-3, IL-6, IL-11 or GM-CSF. When utilizing such a combination therapy, the cytokines may be combined in a single formulation or may be administered in separate formulations. Methods of formulation are well known in the art and are disclosed, for example, in *Remington's Pharmaceutical Sciences*, Gennaro, ed., Mack Publishing Co., Easton Pa., 1990, which is incorporated herein by reference. Therapeutic doses of TPO will generally be in the range of 0.1 to 100 µg/kg of patient weight per day, preferably 0.5–50 µg/kg per day, with the exact dose determined by the clinician according to accepted standards, taking into account the nature and severity of the condition to be treated, patient traits, etc. In certain cases, such as when treating patients showing increased sensitivity or requiring prolonged treatment, doses in the range of 0.1–20 µg/kg per day will be indicated. Determination of dose is within the level of ordinary skill in the art. TPO will commonly be administered over a period of up to 28 days following chemotherapy or bone-marrow transplant or until a platelet count of >20,000/mm$^3$, preferably >50,000/mm$^3$, is achieved. More commonly, TPO will be administered over one week or less, often over a period of one to three days. In general, a therapeutically effective amount of TPO is an amount sufficient to produce a clinically significant increase in the proliferation and/or differentiation of lymphoid or myeloid progenitor cells, which will be manifested as an increase in circulating levels of mature cells (e.g. platelets or neutrophils). Treatment of platelet disorders will thus be continued until a platelet count of at least 20,000/mm$^3$, preferably 50,000/mm$^3$, is reached. TPO can also be administered in combination with other cytokines such as IL-3, -6 and -11; stem cell factor; erythropoietin; G-CSF and GM-CSF. Within regimens of combination therapy, daily doses of other cytokines will in general be: EPO, ≦150 U/kg; GM-CSF, 5–15 µg/kg; IL-3, 1–5 µg/kg; and G-CSF, 1–25 µg/kg. Combination therapy with EPO, for example, is indicated in anemic patients with low EPO levels.

TPO is also a valuable tool for the in vitro study of the differentiation and development of hematopoietic cells, such as for elucidating the mechanisms of cell differentiation and for determining the lineages of mature cells, and may also find utility as a proliferative agent in cell culture.

TPO can also be used ex vivo, such as in autologous marrow culture. Briefly, bone marrow is removed from a patient prior to chemotherapy and treated with TPO, optionally in combination with one or more other cytokines. The treated marrow is then returned to the patient after chemotherapy to speed the recovery of the marrow. In addition, TPO can also be used for the ex vivo expansion of marrow or peripheral blood progenitor (PBPC) cells. Prior to chemotherapy treatment, marrow can be stimulated with stem cell factor (SCF) or G-CSF to release early progenitor cells into peripheral circulation. These progenitors can be collected and concentrated from peripheral blood and then treated in culture with TPO, optionally in combination with one or more other cytokines, including but not limited to SCF, G-CSF, IL-3, GM-CSF, IL-6 or IL-11, to differentiate and proliferate into high-density megakaryocyte cultures, which can then be returned to the patient following high-dose chemotherapy.

The invention is further illustrated by the following non-limiting examples.

EXAMPLES

Example 1

A human t-PA signal sequence was modified by a polymerase chain reaction using oligonucleotide primers ZC7367 (SEQ ID NO:6) and ZC7738 (SEQ ID NO:7) and plasmid Thr102 (disclosed in WIPO publication WO 93/13208) as template. Ten ng of template DNA was combined with 5 µl of 2 mM dNTPs, 5 µl 10×Taq buffer (Boehringer Mannheim, Indianapolis, Ind.), 0.2 µl Taq DNA polymerase (Boehringer Mannheim), 40 pmole of each primer, and $H_2O$ to 50 µl. The mixture was incubated for 15 cycles of 95° C., 1 minute; 50° C., 2 minutes; and 72° C., 1 minute; followed by a final 10 minute incubation at 72° C. DNA was extracted with phenol/$CHCl_3$, precipitated with isopropanol at –20 C. overnight, and resuspended in 30 µl $H_2O$. Ten µl of the DNA was digested with BglII and EcoRI. The digested DNA was electrophoresed on a 2.2% agarose gel. The region of the gel corresponding to 124 bp was cut out and placed in a 0.5 ml microcentrifuge tube with a hole in the bottom on a mat of aquarium filter floss. The tube was placed in an empty 1.5 ml tube, and the assembly was centrifuged to extract the DNA from the gel. Two µg of glycogen was added to the extracted liquid, salt concentration was adjusted to 0.2M NaCl, and the DNA was precipitated by overnight incubation with ethanol at –20° C. The modified sequence encoded a human t-PA secretory peptide in which the Arg residue at -7 was replaced with Glu, and the Ala residue at -2 was replaced with Arg.

To introduce a BglII site into the 5' end of the mouse TPO DNA sequence, pZGmpl-1081 (deposited under the terms of the Budapest Treaty on Feb. 14, 1994 with American Type Culture Collection, 12301 Parklawn Drive, Rockville, Md. as assigned accession number 69566) was mutagenized by PCR. Mutagenesis was carried out using oligonucleotide primers ZC7365 (SEQ ID NO:8) and ZC7645 (SEQ ID NO:9). PCR was run for 20 cycles using conditions described above. DNA was phenol/chloroform extracted and precipatated with isopropanol.

The precipitated DNA was resuspended in $H_2O$ and digested with PstI and BglII. A 313 bp fragment was recovered by gel electrophoresis and centrifugation as described above.

To prepare an expression vector, plasmid Zem229R (deposited under the terms of the Budapest Treaty with American Type Culture Collection, 12301 Parklawn Drive, Rockville, Md. on Sep. 28, 1993 as an *E. coli* HB101 transformant and assigned Accession Number 69447) was digested with EcoRI and treated with alkaline phosphatase. The linearized vector was ligated with the t-PA leader sequence (EcoRI-BglII), the 313 bp PstI-BglII TPO fragment, and a PstI-EcoRI fragment encoding amino acid residues 150 through 196 of SEQ ID NO:2. The ligated DNA was used to transform competent DH10b™ *E. coli* cells (GIBCO BRL, Gaithersburg, Md.), which were plated on media containing ampicillin and incubated overnight.

BHK 570 cells (ATCC CRL 10314) were plated in a 24-well dish at a density of 50,000 cells and incubated for about 15 hours. Plasmid DNA (designated TPO100.229R) was prepared from the transformed *E. coli* cells using a Wizard™ prep (Promega Corp., Madison, Wis.). Forty percent of the DNA (20 µl ) was transfected into the BHK 570 cells using a 3:1 liposome formulation of 2,3-dioleyloxy-N-[2(sperminecarboxyamido)ethyl]-N,N-dimethyl-1-propanaminiumtrifluoroacetate and dioleolyphosphatidylethanolamine in water (Lipofectamine™ reagent, GIBCO-BRL). Transfectants were selected in 500 nM methotrexate (MTX) in Dulbecco's modified Eagle's medium (DME; obtained from BioWhittaker, Inc., Walkersville, Md., or Fred Hutchinson Cancer Research Center, Seattle, Wash.) containing 5% heat-inactivated fetal bovine serum (BioWhittaker), 1 mM sodium pyruvate (Irvine Scientific, Santa Ana, Calif.), 2 mM L-glutamine (JRH Biosciences, Lexena, Kans.) and 25 mM HEPES (JRH Biosciences). Average production of TPO from the pool was 69,000–92,000 units (as defined in Example 10) per ml per day. Pools of transfectants and individual clones were then amplified in 10 µM MTX and cloned by dilution. The amplified pool was found to produce 56,000 U/ml/day TPO.

Example 2

A vector for expression and secretion of full-length mouse TPO was constructed. TPO100.229R was digested with EcoRI and PstI, and the 437 bp fragment was isolated by gel electrophoresis and centrifugation as described above. A PstI-EcoRI fragment encoding amino acids 150–379 of SEQ ID NO:2 was prepared, and the two fragments were ligated with Zem229R that had been digested with EcoRI and treated with alkaline phosphatase. The ligation mixture was used to transform competent *E. coli* DH10b cells, which were then plated onto media containing ampicillin and incubated overnight.

Plasmid DNA (designated TPO101.229R) was prepared from the transformed *E. coli* cells and transfected into BHK 570 cells as described above. A pool of transfectants selected in 500 nM MTX produced 30,000 U/ml/day TPO. A pool of transfectants amplified with 10 µM MTX produced 88,000 U/ml.

Example 3

A full-length mouse TPO DNA sequence was mutagenized by PCR to replace the arginine residues at positions 197–198 of SEQ ID NO:2 with glutamine residues. The mutagenized TPO DNA (EcoRI-NotI) was ligated to EcoRI-digested Zem229R with a NotI/EcoRI oligonucleotide linker. The resulting plasmid was designated TPOM3.

Plasmid TPO100.229R was digested with EcoRI and SalI, and a 218 bp fragment encoding the t-PA leader and amino acid residues 45–76 of SEQ ID NO:2 was isolated. A 1188 bp fragment encoding amino acid residues 77–379 of SEQ ID NO:2 and including 3' untranslated DNA was prepared by digesting TPOM3 with SalI and EcoRI. These two fragments were ligated with Zem229R that had been digested with EcoRI and treated with alkaline phosphatase. The ligation mixture was used to transform competent *E. coli* DH10b™ cells, which were then plated onto media containing ampicillin and incubated overnight. The resulting plasmid was designated TPO110.229R.

Example 4

For expression of human TPO, a BglII site was introduced into the DNA sequence at the position of the codon for amino acid residue 22 (Ser) of SEQ ID NO:4. A polymerase chain reaction was carried out using a human TPO cDNA as template and oligonucleotide primers ZC7907 (SEQ ID NO:10) and 7693 (SEQ ID NO:11). Ten ng of template DNA was combined with 5 µl of 2 mM dNTPs, 5 µl 10×Taq buffer (Boehringer Mannheim), 0.2 µl Taq DNA polymerase (Boehringer Mannheim), 40 pmole of each primer, and $H_2O$ to 50 μL. The mixture was incubated for 30 cycles of 95° C., 1 minute; 50° C., 2 minutes; and 72° C., 1 minute, with a final ten minute incubation at 72° C.

The PCR mixture was extracted with phenol/CHCl$_3$, and the DNA was precipitated with isopropanol and resuspended in H$_2$O. The resuspended DNA was digested with BglII and PstI, and a 316 bp fragment was recovered as described above. This fragment encoded amino acid residues 22–126 of SEQ ID NO:4.

A t-PA leader sequence was prepared from TPO100.229R by digesting the plasmid with EcoRI and BglII and isolating the desired fragment (124 bp) by gel electrophoresis and centrifugation.

To construct a human TPO expression vector, a 710 bp PstI-EcoRI fragment encoding amino acid residues 127–353 of SEQ ID NO:4 was isolated and ligated with the PCR-generated fragment, the leader sequence, and Zem229R that had been digested with EcoRI and treated with alkaline phosphatase. The ligated DNA was used to transform competent *E. coli* DH10b™ cells. The plasmid was designated TPO201.229R.

The TPO201 sequence was placed in an expression vector under the control of an adenovirus major late promoter. Plasmid TPO201.229R was digested with EcoRI, and a 1149 bp fragment encoding the t-PA leader and TPO polypeptide was isolated. This DNA fragment was ligated to the vector pDX (disclosed in U.S. Pat. No. 4,959,318) which had been linearized by digestion with EcoRI and treated with alkaline phosphatase to construct plasmid TPO201.pDX.

BHK 570 cells cotransfected with TPO201.pDX and Zem229R and selected in 5 μM methotrexate produced up to 10,000–15,000 units TPO/ml/day.

Example 5

A vector was constructed for expression of a TPO polypeptide ending at amino acid residue 235 of SEQ ID NO:4. The human TPO DNA sequence was mutagenized by PCR to introduce two stop codons and an EcoRI site following the codon for amino acid 235. Ten ng of template DNA was combined with 5 μl of 2 mM dNTPs, 5 μl 10×Taq buffer (Boehringer Mannheim), 0.2 μl Taq DNA polymerase (Boehringer Mannheim), 40 pmole of each primer ZC7910 (SEQ ID NO:12) and ZC7878 (SEQ ID NO:13), and H20 to 50 μl. The mixture was incubated for 30 cycles of 95° C., 1 minute; 50° C., 2 minutes; and 72° C., 1 minute, with a final ten minute incubation at 72° C. DNA was isolated from the reaction mixture and digested with PstI and Eco RI, and a 334 bp fragment encoding amino acid residues 127–235 of SEQ ID NO:4 was recovered as described above. This fragment was cloned into pIC19H and sequenced to confirm its identity.

The expression vector was then prepared. A 440 bp fragment encoding the t-PA leader and amino acid residues 22–126 of SEQ ID NO:4 was isolated from a EcoRI+PstI digest of TPO201.229R. The PCR-generated fragment was isolated from a EcoRI+PstI digest of the pIC19H clone. The two fragments were ligated with Zem229R that had been digested with EcoRI and treated with alkaline phosphatase. The ligated DNA was used to transform competent *E. coli* DH10b™ cells. The plasmid was designated TPO200.229R.

Plasmid TPO200.229R was transfected into BHK 570 cells using Lipfectamine™ essentially as described in Example 1. The cells were plated in 24-well dish at a density of 40,000 cells/well one day prior to transfection. After initial selection in 500 nM MTX, pooled cells produced 1290 U/ml/day TPO. Following amplification in 5 μM MTX, pooled cells produced 2330 U/ml/day TPO. A pool of cells amplified in 50 μM MTX produced 4700 U/ml/day.

A second expression vector was constructed comprising an adenovirus major late promoter, t-PA leader and human TPO 22–235 sequence. Plasmid TPO200.229R was digested with EcoRI, and a 775 bp fragment encoding the t-PA leader and human TPO polypeptide was recovered. This DNA fragment was ligated to the vector pDX which had been linearized by digestion with EcoRI and treated with alkaline phosphatase. The ligated DNA was transformed into *E. coli* MC1061 cells. The plasmid was designated TPO200.pDX.

TPO200.pDX was cotransfected into BHK 570 cells with Zem229R. Cells selected in 500 nM methotrexate produced up to 10,000–15,000 units TPO/ml/day.

Example 6

A vector was constructed for expression of a TPO polypeptide ending at amino acid residue 193 of SEQ ID NO:4. The human TPO DNA sequence was mutagenized by PCR to introduce a stop codon and an EcoRI site following the codon for amino acid 193. Ten ng of template DNA was combined with 5 μl of 2 mM dNTPs, 5 μl 10×Taq buffer (Boehringer Mannheim), 0.2 μl Taq DNA polymerase (Boehringer Mannheim), 40 pmole of each primer ZC8045 (SEQ ID NO:14) and ZC7878 (SEQ ID NO:13), and H$_2$O to 50 μl. The mixture was incubated for 30 cycles of 95° C., 1 minute; 50° C., 2 minutes; and 72° C., 1 minute, with a final ten minute incubation at 72° C. DNA was isolated from the reaction mixture and digested with PstI and Eco RI, and a 204 bp fragment encoding amino acid residues 127–193 of SEQ ID NO:4 was recovered as described above.

To construct the expression vector, the isolated PCR product was ligated with the EcoRI-PstI fragment encoding the t-PA leader and amino acid residues 22–126 of SEQ ID NO:4 (Example 5) and Zem229R that had been digested with EcoRI and treated with alkaline phosphatase. The ligated DNA was used to transform competent *E. coli* DH10b™ cells. The plasmid was designated TPO202.229R.

BHK 570 cells were transfected with TPO202.229R as described above and selected in 500 nM MTX. Pooled cells produced 13,110 U/ml TPO. After amplification in 5 μM MTX, pooled cells produced 20,850 U/ml/day TPO.

The 646 bp EcoRI insert was removed from TPO202.229R and ligated to pDX that had been linearized by digestion with EcoRI and treated with alkaline phosphatase. The resulting vector, designated TPO202.pDX, was cotransfected into BHK 570 cells with Zem229R, or with AAT.229R. Cells cotransfected wtih TPO202.pDX and AAT.229R and amplified with 500 nM MTX produced 20,500 U/ml/day TPO. TPO202.pDX/Zem229R cotransfectants amplified in 500 nM MTX produced 17,000 U/ml/day TPO.

Example 7

The Arg residue at position -5 in the t-PA leader was replaced with a Gln residue. A polymerase chain reaction was carried out using TPO100.229R as template, oligonucleotide primers ZC7367 (SEQ ID NO:6) and ZC7956 (SEQ ID NO:15) and reaction conditions specified in Example 6. DNA was isolated as previously described and digested with EcoRI and BglII, and a 124 bp fragment encoding the modified t-PA leader was recovered.

To construct an expression vector, the 124 bp PCR product was ligated with a BglII-EcoRI TPO-encoding fragment from TPO201.229R and Zem229R that had been digested with EcoRI and treated with alkaline phosphatase. The ligated DNA was used to transform competent *E. coli* DH10b™ cells. The plasmid was designated TPO251.229R.

BHK 570 cells were plated on a 24-well plate at 40,000 cells/well one day prior to transfection. After transfection with TPO251.229R and selection in MTX, pooled cells produced 1340 U/ml TPO. Following amplification in 5 µM MTX, pooled cells produced 3940 U/ml TPO.

Example 8

A vector was constructed for the expression of a human TPO polypeptide ending at residue 235 of SEQ ID NO:4 with the modified t-PA leader of Example 7. Each of TPO251.229R and TPO200.229R was digested with PstI and EcoRI. Fragments of 441 bp and 335 bp, respectively, were recovered. The two fragments were ligated with Zem229R that had been digested with EcoRI and treated with alkaline phosphatase. The ligated DNA was used to transform competent *E. coil* MC1061 cells. The plasmid was designated TPO250.229R.

Plasmid TPO250.229R was transfected into BHK 570 cells. Pooled cells selected in 500 nM MTX produced 870 U/ml/day TPO. A pool of cells amplified in 50 µM MTX produced 11,600 U/ml/day.

The 775 bp EcoRI insert was removed from TPO250.229R and ligated with pDX that had been linearized with EcoRI and treated with alkaline phosphatase. The resulting vector was designated TPO250.pDX. BHK 570 cells were cotransfected with TPO250.pDX and Zem229R. A pool of cells amplified in 5 µM MTX produced 21,900 U/ml/day TPO.

Example 9

A vector was constructed for the expression of a human TPO polypeptide ending at residue 193 of SEQ ID NO:4 with the modified t-PA leader of Example 7. Each of TPO250.229R and TPO202.229R was digested with PstI and EcoRI. Fragments of 441 bp and 205 bp, respectively, were recovered. The two fragments were ligated with Zem229R that had been digested with EcoRI and treated with alkaline phosphatase. The ligated DNA was used to transform competent *E. coli* MC1061 cells. The plasmid was designated TPO252.229R.

TPO252.229R was transfected in BHK 570 cells. After selection in 500 nM MTX, pooled cells produced 8500 U/ml TPO. Following amplification in 5 µM MTX, pooled cells produced 31,300 U/ml/day.

The TPO252 sequence was isolated from plasmid TPO252.229R and ligated with EcoRI-digested, alkaline phosphatase-treated pDX to construct TPO252.pDX. Cells were cotransfected with TPO252.pDX and Zem229R. After amplification in 500 nM MTX, individual clones produced up to about 30,000 U/ml/day TPO.

Example 10

Units of TPO activity were determined by assaying mitogenic activity on a TPO-dependent cell line. A BHK 570 cell line transfected with the mouse TPO expression vector pZGmpl-1081 was grown in serum-free medium. Conditioned culture medium was collected, and an asymptotic mitogenic activity curve was generated using this standard solution. The target cells were BaF3/MPLR1.1 cells (IL-3-dependent cells expressing a stably transfected Type I mouse MPL receptor; deposited Sep. 28, 1994 under the terms of the Budapest Treaty with American Type Culture Collection, 12301 Parklawn Drive, Rockville, Md. and assigned accession number CRL 11723). The point of ½ maximal activity (average of 16 curves) was assigned the value of 50 U/ml. The original standard solution was calculated to contain 26,600 U/ml mouse TPO.

For test samples, a culture supernatant or purified protein preparation was diluted in RPMI 1640 medium supplemented with 57 µM 2-mercaptoethanol, 2 mM L-glutamine, 1 mM sodium pyruvate, PSN antibiotic mixture, 10 mM HEPES and 10% heat inactivated fetal bovine serum, generally using 8–24 dilutions. Briefly, 100 µl of diluted test sample or standard sample and 100 µl BaF3 cells (final cell number added about 10,000 cells/well) were combined in wells of a 96 well plate. Internal standards included eight 2-fold dilutions of 100 U/ml mouse TPO for mouse TPO assays, or eight 2-fold dilutions of 150 U/ml mouse TPO for human TPO assays. To each well was added 2 µl $^3$H-thymidine (1 µCi/µl; Amersham), and the plates were incubated overnight at 37° C.

The contents of each well of each plate were transferred to a filter/plate using a Packard apparatus. The filters were washed 8 times with water, and the filters were dried and counted. Units of TPO activity in each sample well were determined by comparison to the standard curve.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A DNA construct comprising:

a first DNA segment encoding a polypeptide fusion, said fusion comprising an amino-terminal secretory peptide joined to a thrombopoietin (TPO) polypeptide, the joined peptide and polypeptide defining a proteolytic cleavage site at their junction; and one or more additional DNA segments operably linked to said first DNA segment so as to provide for its transcription, wherein said secretory peptide is selected from the group consisting of:
native mammalian tissue plasminogen activator (t-PA) secretory peptides; and
mammalian t-PA secretory peptides modified to enhance proteolytic cleavage at said junction.

2. A DNA construct according to claim 1 wherein said secretory peptide is a human t-PA secretory peptide.

3. A DNA construct according to claim 1 wherein said secretory peptide consists of a sequence of amino acid residues as shown in SEQ ID NO:5 wherein Xaa(29), Xaa(31) and Xaa(33) are individually any amino acid and Xaa(34) is Ala, Arg or Lys.

4. A DNA construct according to claim 3 wherein Xaa(29) and Xaa(31) are individually any amino acid except Lys, Arg or His.

5. A DNA construct according to claim 3 wherein Xaa(33) is Gly.

6. A DNA construct according to claim 3 wherein Xaa(34) is Arg or Lys.

7. A DNA construct according to claim 3 wherein Xaa(29) and Xaa(31) are individually Asp, Glu, Gln, Gly or Ala; Xaa(33) is Gly; and Xaa(34) is Arg.

8. A DNA construct according to claim 3 wherein Xaa(29) is Arg or Glu, Xaa(31) is Arg or Gln, Xaa(33) is Gly, and Xaa(34) is Arg, subject to the limitation that at least one of Xaa(29) and Xaa(31) is not Arg.

9. A DNA construct according to claim 1 wherein said TPO polypeptide consists of from 144 to 335 amino acid residues.

10. A DNA construct according to claim 1 wherein said TPO polypeptide consists of from 144 to 191 amino acid residues.

11. A DNA construct according to claim 1 wherein said TPO polypeptide consists of a sequence of amino acids selected from the group consisting of:

Ser(22) to Val(173) of SEQ ID NO:4;
Ser(22) to Arg(185) of SEQ ID NO:4;
Ser(22) to Asn(193) of SEQ ID NO:4;
Ser(22) to Phe(207) of SEQ ID NO:4; and
Ser(22) to Gln(235) of SEQ ID NO:4.

12. A DNA construct according to claim 1 wherein said TPO polypeptide is a human TPO polypeptide.

13. A DNA construct according to claim 1 further comprising a selectable marker.

14. A DNA construct comprising a first DNA segment encoding a polypeptide fusion consisting essentially of an amino-terminal secretory peptide as shown in SEQ ID NO:5 wherein Xaa(29) is Arg or Glu, Xaa(31) is Arg or Gln, Xaa(33) is Gly, and Xaa(34) is Ala or Arg, joined directly to a TPO polypeptide of from 144 to 335 amino acids, wherein said first DNA segment is operably linked to one or more additional DNA segments that provide for its transcription.

15. A DNA construct according to claim 14 wherein said TPO polypeptide consists of from 144 to 191 amino acid residues.

16. A DNA construct according to claim 14 wherein said TPO polypeptide is a human TPO polypeptide.

17. A DNA construct according to claim 14 wherein said TPO polypeptide consists of a sequence of amino acids selected from the group consisting of:

Ser(22) to Val(173) of SEQ ID NO:4;
Ser(22) to Arg(185) of SEQ ID NO:4;

Ser(22) to Asn(193) of SEQ ID NO:4;

Ser(22) to Phe(207) of SEQ ID NO:4; and

Ser(22) to Gln(235) of SEQ ID NO:4.

18. A DNA construct according to claim 14 further comprising a selectable marker.

19. A cultured eukaryotic cell containing a DNA construct comprising:

a first DNA segment encoding a polypeptide fusion, said fusion comprising an amino-terminal secretory peptide joined to a TPO polypeptide, the fused sequences defining a proteolytic cleavage site at their junction; and one or more additional DNA segments operably linked to said first DNA segment so as to provide for its transcription, wherein said secretory peptide is selected from the group consisting of:

native mammalian t-PA secretory peptides; and mammalian t-PA secretory peptides modified to enhance proteolytic cleavage at said junction.

20. A yeast cell according to claim 19.

21. A yeast cell according to claim 20 wherein said cell is a *Saccharomyces cerevisiae* cell.

22. A yeast cell according to claim 20 wherein said cell is a *Pichia pastoris* cell.

23. A cultured mammalian cell according to claim 19.

24. A mammalian cell according to claim 23 which is a rodent cell.

25. A mammalian cell according to claim 23 which is a kidney cell.

26. A method for producing a thrombopoietin polypeptide comprising the steps of:

(a) culturing a eukaryotic cell containing a DNA construct comprising a first DNA segment encoding a polypeptide fusion, said fusion comprising an amino-terminal secretory peptide joined to a thrombopoietin (TPO) polypeptide, the joined peptide and polypeptide defining a proteolytic cleavage site at their junction; and one or more additional DNA segments operably linked to said first DNA segment so as to provide for its transcription, wherein said secretory peptide is selected from the group consisting of:

native mammalian tissue plasminogen activator (t-PA) secretory peptides; and mammalian t-PA secretory peptides modified to enhance proteolytic cleavage at said junction, wherein said cell expresses said first DNA segment and said TPO polypeptide is secreted from the cell; and (b) selectively recovering said TPO polypeptide.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 1486 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
    ( A ) NAME/KEY: CDS
    ( B ) LOCATION: 105..1241

( x i ) SEQUENCE DESCRIPTION: SEQ ID NO:1:

```
CCTCGTGCCG GTCCTGAGGC CCTTCTCCAC CCGGACAGAG TCCTTGGCCC ACCTCTCTCC        60

CACCCGACTC TGCCGAAAGA AGCACAGAAG CTCAAGCCGC CTCC ATG GCC CCA GGA        116
                                              Met Ala Pro Gly
                                                1

AAG ATT CAG GGG AGA GGC CCC ATA CAG GGA GCC ACT TCA GTT AGA CAC         164
Lys Ile Gln Gly Arg Gly Pro Ile Gln Gly Ala Thr Ser Val Arg His
  5              10                  15                  20

CTG GCC AGA ATG GAG CTG ACT GAT TTG CTC CTG GCG GCC ATG CTT CTT         212
Leu Ala Arg Met Glu Leu Thr Asp Leu Leu Leu Ala Ala Met Leu Leu
                 25                  30                  35

GCA GTG GCA AGA CTA ACT CTG TCC AGC CCC GTA GCT CCT GCC TGT GAC         260
Ala Val Ala Arg Leu Thr Leu Ser Ser Pro Val Ala Pro Ala Cys Asp
             40                  45                  50

CCC AGA CTC CTA AAT AAA CTG CTG CGT GAC TCC CAC CTC CTT CAC AGC         308
Pro Arg Leu Leu Asn Lys Leu Leu Arg Asp Ser His Leu Leu His Ser
         55                  60                  65

CGA CTG AGT CAG TGT CCC GAC GTC GAC CCT TTG TCT ATC CCT GTT CTG         356
Arg Leu Ser Gln Cys Pro Asp Val Asp Pro Leu Ser Ile Pro Val Leu
     70                  75                  80

CTG CCT GCT GTG GAC TTT AGC CTG GGA GAA TGG AAA ACC CAG ACG GAA         404
Leu Pro Ala Val Asp Phe Ser Leu Gly Glu Trp Lys Thr Gln Thr Glu
 85                  90                  95                 100

CAG AGC AAG GCA CAG GAC ATT CTA GGG GCA GTG TCC CTT CTA CTG GAG         452
Gln Ser Lys Ala Gln Asp Ile Leu Gly Ala Val Ser Leu Leu Leu Glu
                 105                 110                 115

GGA GTG ATG GCA GCA CGA GGA CAG TTG GAA CCC TCC TGC CTC TCA TCC         500
Gly Val Met Ala Ala Arg Gly Gln Leu Glu Pro Ser Cys Leu Ser Ser
             120                 125                 130

CTC CTG GGA CAG CTT TCT GGG CAG GTT CGC CTC CTC TTG GGG GCC CTG         548
Leu Leu Gly Gln Leu Ser Gly Gln Val Arg Leu Leu Leu Gly Ala Leu
         135                 140                 145

CAG GGC CTC CTA GGA ACC CAG CTT CCT CTA CAG GGC AGG ACC ACA GCT         596
Gln Gly Leu Leu Gly Thr Gln Leu Pro Leu Gln Gly Arg Thr Thr Ala
     150                 155                 160

CAC AAG GAC CCC AAT GCC CTC TTC TTG AGC TTG CAA CAA CTG CTT CGG         644
His Lys Asp Pro Asn Ala Leu Phe Leu Ser Leu Gln Gln Leu Leu Arg
165                 170                 175                 180

GGA AAG GTG CGC TTC CTG CTT CTG GTA GAA GGT CCC ACC CTC TGT GTC         692
Gly Lys Val Arg Phe Leu Leu Leu Val Glu Gly Pro Thr Leu Cys Val
                 185                 190                 195

AGA CGG ACC CTG CCA ACC ACA GCT GTC CCA AGC AGT ACT TCT CAA CTC         740
Arg Arg Thr Leu Pro Thr Thr Ala Val Pro Ser Ser Thr Ser Gln Leu
             200                 205                 210

CTC ACA CTA AAC AAG TTC CCA AAC AGG ACT TCT GGA TTG TTG GAG ACG         788
Leu Thr Leu Asn Lys Phe Pro Asn Arg Thr Ser Gly Leu Leu Glu Thr
         215                 220                 225

AAC TTC AGT GTC ACA GCC AGA ACT GCT GGC CCT GGA CTT CTG AGC AGG         836
Asn Phe Ser Val Thr Ala Arg Thr Ala Gly Pro Gly Leu Leu Ser Arg
     230                 235                 240

CTT CAG GGA TTC AGA GTC AAG ATT ACT CCT GGT CAG CTA AAT CAA ACC         884
Leu Gln Gly Phe Arg Val Lys Ile Thr Pro Gly Gln Leu Asn Gln Thr
245                 250                 255                 260

TCC AGG TCC CCA GTC CAA ATC TCT GGA TAC CTG AAC AGG ACA CAC GGA         932
Ser Arg Ser Pro Val Gln Ile Ser Gly Tyr Leu Asn Arg Thr His Gly
                 265                 270                 275
```

```
CCT GTG AAT GGA ACT CAT GGG CTC TTT GCT GGA ACC TCA CTT CAG ACC        980
Pro Val Asn Gly Thr His Gly Leu Phe Ala Gly Thr Ser Leu Gln Thr
        280                     285                 290

CTG GAA GCC TCA GAC ATC TCG CCC GGA GCT TTC AAC AAA GGC TCC CTG       1028
Leu Glu Ala Ser Asp Ile Ser Pro Gly Ala Phe Asn Lys Gly Ser Leu
        295                     300                 305

GCA TTC AAC CTC CAG GGT GGA CTT CCT CCT TCT CCA AGC CTT GCT CCT       1076
Ala Phe Asn Leu Gln Gly Gly Leu Pro Pro Ser Pro Ser Leu Ala Pro
        310                     315                 320

GAT GGA CAC ACA CCC TTC CCT CCT TCA CCT GCC TTG CCC ACC ACC CAT       1124
Asp Gly His Thr Pro Phe Pro Pro Ser Pro Ala Leu Pro Thr Thr His
325                     330                 335                 340

GGA TCT CCA CCC CAG CTC CAC CCC CTG TTT CCT GAC CCT TCC ACC ACC       1172
Gly Ser Pro Pro Gln Leu His Pro Leu Phe Pro Asp Pro Ser Thr Thr
                345                 350                 355

ATG CCT AAC TCT ACC GCC CCT CAT CCA GTC ACA ATG TAC CCT CAT CCC       1220
Met Pro Asn Ser Thr Ala Pro His Pro Val Thr Met Tyr Pro His Pro
        360                     365                 370

AGG AAT TTG TCT CAG GAA ACA TAGCGCGGGC ACTGGCCCAG TGAGCGTCTG          1271
Arg Asn Leu Ser Gln Glu Thr
        375

CAGCTTCTCT CGGGGACAAG CTTCCCCAGG AAGGCTGAGA GGCAGCTGCA TCTGCTCCAG     1331

ATGTTCTGCT TTCACCTAAA AGGCCCTGGG GAAGGGATAC ACAGCACTGG AGATTGTAAA     1391

ATTTAGGAG CTATTTTTTT TTAACCTATC AGCAATATTC ATCAGAGCAG CTAGCGATCT      1451

TTGGTCTATT TTCGGTATAA ATTTGAAAAT CACTA                                1486
```

( 2 ) INFORMATION FOR SEQ ID NO:2:

( i ) SEQUENCE CHARACTERISTICS:
( A ) LENGTH: 379 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Ala Pro Gly Lys Ile Gln Gly Arg Gly Pro Ile Gln Gly Ala Thr
1               5                   10                  15

Ser Val Arg His Leu Ala Arg Met Glu Leu Thr Asp Leu Leu Leu Ala
            20                  25                  30

Ala Met Leu Leu Ala Val Ala Arg Leu Thr Leu Ser Ser Pro Val Ala
        35                  40                  45

Pro Ala Cys Asp Pro Arg Leu Leu Asn Lys Leu Leu Arg Asp Ser His
    50                  55                  60

Leu Leu His Ser Arg Leu Ser Gln Cys Pro Asp Val Asp Pro Leu Ser
65                  70                  75                  80

Ile Pro Val Leu Leu Pro Ala Val Asp Phe Ser Leu Gly Glu Trp Lys
                85                  90                  95

Thr Gln Thr Glu Gln Ser Lys Ala Gln Asp Ile Leu Gly Ala Val Ser
            100                 105                 110

Leu Leu Leu Glu Gly Val Met Ala Ala Arg Gly Gln Leu Glu Pro Ser
        115                 120                 125

Cys Leu Ser Ser Leu Leu Gly Gln Leu Ser Gly Gln Val Arg Leu Leu
    130                 135                 140

Leu Gly Ala Leu Gln Gly Leu Leu Gly Thr Gln Leu Pro Leu Gln Gly
145                 150                 155                 160

Arg Thr Thr Ala His Lys Asp Pro Asn Ala Leu Phe Leu Ser Leu Gln
```

|     |     |     |     | 165 |     |     |     |     | 170 |     |     |     |     | 175 |     |
| --- | --- | --- | --- | --- | --- | --- | --- | --- | --- | --- | --- | --- | --- | --- | --- |
| Gln | Leu | Leu | Arg<br>180 | Gly | Lys | Val | Arg | Phe<br>185 | Leu | Leu | Leu | Val | Glu<br>190 | Gly | Pro |
| Thr | Leu | Cys<br>195 | Val | Arg | Arg | Thr | Leu<br>200 | Pro | Thr | Thr | Ala | Val<br>205 | Pro | Ser | Ser |
| Thr | Ser<br>210 | Gln | Leu | Leu | Thr | Leu<br>215 | Asn | Lys | Phe | Pro | Asn<br>220 | Arg | Thr | Ser | Gly |
| Leu<br>225 | Leu | Glu | Thr | Asn | Phe<br>230 | Ser | Val | Thr | Ala | Arg<br>235 | Thr | Ala | Gly | Pro | Gly<br>240 |
| Leu | Leu | Ser | Arg | Leu<br>245 | Gln | Gly | Phe | Arg | Val<br>250 | Lys | Ile | Thr | Pro | Gly<br>255 | Gln |
| Leu | Asn | Gln | Thr<br>260 | Ser | Arg | Ser | Pro | Val<br>265 | Gln | Ile | Ser | Gly | Tyr<br>270 | Leu | Asn |
| Arg | Thr | His<br>275 | Gly | Pro | Val | Asn | Gly<br>280 | Thr | His | Gly | Leu | Phe<br>285 | Ala | Gly | Thr |
| Ser | Leu<br>290 | Gln | Thr | Leu | Glu | Ala<br>295 | Ser | Asp | Ile | Ser | Pro<br>300 | Gly | Ala | Phe | Asn |
| Lys<br>305 | Gly | Ser | Leu | Ala | Phe<br>310 | Asn | Leu | Gln | Gly | Gly<br>315 | Leu | Pro | Pro | Ser | Pro<br>320 |
| Ser | Leu | Ala | Pro | Asp<br>325 | Gly | His | Thr | Pro | Phe<br>330 | Pro | Pro | Ser | Pro | Ala<br>335 | Leu |
| Pro | Thr | Thr | His<br>340 | Gly | Ser | Pro | Pro | Gln<br>345 | Leu | His | Pro | Leu | Phe<br>350 | Pro | Asp |
| Pro | Ser | Thr<br>355 | Thr | Met | Pro | Asn | Ser<br>360 | Thr | Ala | Pro | His | Pro<br>365 | Val | Thr | Met |
| Tyr | Pro<br>370 | His | Pro | Arg | Asn | Leu<br>375 | Ser | Gln | Glu | Thr |     |     |     |     |     |

( 2 ) INFORMATION FOR SEQ ID NO:3:

( i ) SEQUENCE CHARACTERISTICS:
        ( A ) LENGTH: 1062 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..1059

( x i ) SEQUENCE DESCRIPTION: SEQ ID NO:3:

| ATG | GAG | CTG | ACT | GAA | TTG | CTC | CTC | GTG | GTC | ATG | CTT | CTC | CTA | ACT | GCA | 48 |
| --- | --- | --- | --- | --- | --- | --- | --- | --- | --- | --- | --- | --- | --- | --- | --- | --- |
| Met<br>1 | Glu | Leu | Thr | Glu<br>5 | Leu | Leu | Leu | Val | Val<br>10 | Met | Leu | Leu | Leu | Thr<br>15 | Ala |     |
| AGG | CTA | ACG | CTG | TCC | AGC | CCG | GCT | CCT | CCT | GCT | TGT | GAC | CTC | CGA | GTC | 96 |
| Arg | Leu | Thr | Leu<br>20 | Ser | Ser | Pro | Ala | Pro<br>25 | Pro | Ala | Cys | Asp | Leu<br>30 | Arg | Val |     |
| CTC | AGT | AAA | CTG | CTT | CGT | GAC | TCC | CAT | GTC | CTT | CAC | AGC | AGA | CTG | AGC | 144 |
| Leu | Ser | Lys<br>35 | Leu | Leu | Arg | Asp | Ser<br>40 | His | Val | Leu | His | Ser<br>45 | Arg | Leu | Ser |     |
| CAG | TGC | CCA | GAG | GTT | CAC | CCT | TTG | CCT | ACA | CCT | GTC | CTG | CTG | CCT | GCT | 192 |
| Gln | Cys<br>50 | Pro | Glu | Val | His | Pro<br>55 | Leu | Pro | Thr | Pro | Val<br>60 | Leu | Leu | Pro | Ala |     |
| GTG | GAC | TTT | AGC | TTG | GGA | GAA | TGG | AAA | ACC | CAG | ATG | GAG | GAG | ACC | AAG | 240 |
| Val<br>65 | Asp | Phe | Ser | Leu | Gly<br>70 | Glu | Trp | Lys | Thr | Gln<br>75 | Met | Glu | Glu | Thr | Lys<br>80 |     |
| GCA | CAG | GAC | ATT | CTG | GGA | GCA | GTG | ACC | CTT | CTG | CTG | GAG | GGA | GTG | ATG | 288 |
| Ala | Gln | Asp | Ile | Leu<br>85 | Gly | Ala | Val | Thr | Leu | Leu | Leu | Glu | Gly | Val | Met |     |

|  |  |  |  |  |  |  |  |  |  |  |  |  |  |  |  |
|---|---|---|---|---|---|---|---|---|---|---|---|---|---|---|---|
|  |  |  |  | 85 |  |  |  | 90 |  |  |  | 95 |  |  |  |
| GCA | GCA | CGG | GGA | CAA | CTG | GGA | CCC | ACT | TGC | CTC | TCA | TCC | CTC | CTG | GGG | 336
| Ala | Ala | Arg | Gly | Gln | Leu | Gly | Pro | Thr | Cys | Leu | Ser | Ser | Leu | Leu | Gly |
|  |  |  | 100 |  |  |  | 105 |  |  |  | 110 |  |  |  |  |
| CAG | CTT | TCT | GGA | CAG | GTC | CGT | CTC | CTC | CTT | GGG | GCC | CTG | CAG | AGC | CTC | 384
| Gln | Leu | Ser | Gly | Gln | Val | Arg | Leu | Leu | Leu | Gly | Ala | Leu | Gln | Ser | Leu |
|  |  | 115 |  |  |  | 120 |  |  |  |  | 125 |  |  |  |  |
| CTT | GGA | ACC | CAG | CTT | CCT | CCA | CAG | GGC | AGG | ACC | ACA | GCT | CAC | AAG | GAT | 432
| Leu | Gly | Thr | Gln | Leu | Pro | Pro | Gln | Gly | Arg | Thr | Thr | Ala | His | Lys | Asp |
|  | 130 |  |  |  | 135 |  |  |  |  | 140 |  |  |  |  |  |
| CCC | AAT | GCC | ATC | TTC | CTG | AGC | TTC | CAA | CAC | CTG | CTC | CGA | GGA | AAG | GTG | 480
| Pro | Asn | Ala | Ile | Phe | Leu | Ser | Phe | Gln | His | Leu | Leu | Arg | Gly | Lys | Val |
| 145 |  |  |  | 150 |  |  |  | 155 |  |  |  | 160 |  |  |  |
| CGT | TTC | CTG | ATG | CTT | GTA | GGA | GGG | TCC | ACC | CTC | TGC | GTC | AGG | CGG | GCC | 528
| Arg | Phe | Leu | Met | Leu | Val | Gly | Gly | Ser | Thr | Leu | Cys | Val | Arg | Arg | Ala |
|  |  |  |  | 165 |  |  |  | 170 |  |  |  | 175 |  |  |
| CCA | CCC | ACC | ACA | GCT | GTC | CCC | AGC | AGA | ACC | TCT | CTA | GTC | CTC | ACA | CTG | 576
| Pro | Pro | Thr | Thr | Ala | Val | Pro | Ser | Arg | Thr | Ser | Leu | Val | Leu | Thr | Leu |
|  |  |  | 180 |  |  |  |  | 185 |  |  |  |  | 190 |  |  |
| AAC | GAG | CTC | CCA | AAC | AGG | ACT | TCT | GGA | TTG | TTG | GAG | ACA | AAC | TTC | ACT | 624
| Asn | Glu | Leu | Pro | Asn | Arg | Thr | Ser | Gly | Leu | Leu | Glu | Thr | Asn | Phe | Thr |
|  |  | 195 |  |  |  |  | 200 |  |  |  |  | 205 |  |  |  |
| GCC | TCA | GCC | AGA | ACT | ACT | GGC | TCT | GGG | CTT | CTG | AAG | TGG | CAG | CAG | GGA | 672
| Ala | Ser | Ala | Arg | Thr | Thr | Gly | Ser | Gly | Leu | Leu | Lys | Trp | Gln | Gln | Gly |
|  | 210 |  |  |  |  | 215 |  |  |  |  | 220 |  |  |  |  |
| TTC | AGA | GCC | AAG | ATT | CCT | GGT | CTG | CTG | AAC | CAA | ACC | TCC | AGG | TCC | CTG | 720
| Phe | Arg | Ala | Lys | Ile | Pro | Gly | Leu | Leu | Asn | Gln | Thr | Ser | Arg | Ser | Leu |
| 225 |  |  |  |  | 230 |  |  |  |  | 235 |  |  |  |  | 240 |
| GAC | CAA | ATC | CCC | GGA | TAC | CTG | AAC | AGG | ATA | CAC | GAA | CTC | TTG | AAT | GGA | 768
| Asp | Gln | Ile | Pro | Gly | Tyr | Leu | Asn | Arg | Ile | His | Glu | Leu | Leu | Asn | Gly |
|  |  |  |  | 245 |  |  |  |  | 250 |  |  |  |  | 255 |  |
| ACT | CGT | GGA | CTC | TTT | CCT | GGA | CCC | TCA | CGC | AGG | ACC | CTA | GGA | GCC | CCG | 816
| Thr | Arg | Gly | Leu | Phe | Pro | Gly | Pro | Ser | Arg | Arg | Thr | Leu | Gly | Ala | Pro |
|  |  |  | 260 |  |  |  |  | 265 |  |  |  |  | 270 |  |  |
| GAC | ATT | TCC | TCA | GGA | ACA | TCA | GAC | ACA | GGC | TCC | CTG | CCA | CCC | AAC | CTC | 864
| Asp | Ile | Ser | Ser | Gly | Thr | Ser | Asp | Thr | Gly | Ser | Leu | Pro | Pro | Asn | Leu |
|  |  | 275 |  |  |  |  | 280 |  |  |  |  | 285 |  |  |  |
| CAG | CCT | GGA | TAT | TCT | CCT | TCC | CCA | ACC | CAT | CCT | CCT | ACT | GGA | CAG | TAT | 912
| Gln | Pro | Gly | Tyr | Ser | Pro | Ser | Pro | Thr | His | Pro | Pro | Thr | Gly | Gln | Tyr |
|  | 290 |  |  |  |  | 295 |  |  |  |  | 300 |  |  |  |  |
| ACG | CTC | TTC | CCT | CTT | CCA | CCC | ACC | TTG | CCC | ACC | CCT | GTG | GTC | CAG | CTC | 960
| Thr | Leu | Phe | Pro | Leu | Pro | Pro | Thr | Leu | Pro | Thr | Pro | Val | Val | Gln | Leu |
| 305 |  |  |  |  | 310 |  |  |  |  | 315 |  |  |  |  | 320 |
| CAC | CCC | CTG | CTT | CCT | GAC | CCT | TCT | GCT | CCA | ACG | CCC | ACC | CCT | ACC | AGC | 1008
| His | Pro | Leu | Leu | Pro | Asp | Pro | Ser | Ala | Pro | Thr | Pro | Thr | Pro | Thr | Ser |
|  |  |  |  | 325 |  |  |  |  | 330 |  |  |  |  | 335 |  |
| CCT | CTT | CTA | AAC | ACA | TCC | TAC | ACC | CAC | TCC | CAG | AAT | CTG | TCT | CAG | GAA | 1056
| Pro | Leu | Leu | Asn | Thr | Ser | Tyr | Thr | His | Ser | Gln | Asn | Leu | Ser | Gln | Glu |
|  |  |  | 340 |  |  |  |  | 345 |  |  |  |  | 350 |  |  |
| GGG | TAA |  |  |  |  |  |  |  |  |  |  |  |  |  |  | 1062
| Gly |  |  |  |  |  |  |  |  |  |  |  |  |  |  |  |

( 2 ) INFORMATION FOR SEQ ID NO:4:

( i ) SEQUENCE CHARACTERISTICS:
        ( A ) LENGTH: 353 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Glu  Leu  Thr  Glu  Leu  Leu  Leu  Val  Val  Met  Leu  Leu  Leu  Thr  Ala
 1              5                   10                            15

Arg  Leu  Thr  Leu  Ser  Ser  Pro  Ala  Pro  Ala  Cys  Asp  Leu  Arg  Val
               20                   25                  30

Leu  Ser  Lys  Leu  Leu  Arg  Asp  Ser  His  Val  Leu  His  Ser  Arg  Leu  Ser
          35                       40                      45

Gln  Cys  Pro  Glu  Val  His  Pro  Leu  Pro  Thr  Pro  Val  Leu  Leu  Pro  Ala
     50                        55                      60

Val  Asp  Phe  Ser  Leu  Gly  Glu  Trp  Lys  Thr  Gln  Met  Glu  Glu  Thr  Lys
 65                       70                  75                            80

Ala  Gln  Asp  Ile  Leu  Gly  Ala  Val  Thr  Leu  Leu  Leu  Glu  Gly  Val  Met
                    85                       90                            95

Ala  Ala  Arg  Gly  Gln  Leu  Gly  Pro  Thr  Cys  Leu  Ser  Ser  Leu  Leu  Gly
               100                      105                      110

Gln  Leu  Ser  Gly  Gln  Val  Arg  Leu  Leu  Leu  Gly  Ala  Leu  Gln  Ser  Leu
               115                 120                      125

Leu  Gly  Thr  Gln  Leu  Pro  Pro  Gln  Gly  Arg  Thr  Thr  Ala  His  Lys  Asp
     130                      135                 140

Pro  Asn  Ala  Ile  Phe  Leu  Ser  Phe  Gln  His  Leu  Leu  Arg  Gly  Lys  Val
145                           150                 155                      160

Arg  Phe  Leu  Met  Leu  Val  Gly  Gly  Ser  Thr  Leu  Cys  Val  Arg  Arg  Ala
               165                      170                      175

Pro  Pro  Thr  Thr  Ala  Val  Pro  Ser  Arg  Thr  Ser  Leu  Val  Leu  Thr  Leu
               180                 185                      190

Asn  Glu  Leu  Pro  Asn  Arg  Thr  Ser  Gly  Leu  Leu  Glu  Thr  Asn  Phe  Thr
          195                      200                 205

Ala  Ser  Ala  Arg  Thr  Thr  Gly  Ser  Gly  Leu  Leu  Lys  Trp  Gln  Gln  Gly
     210                      215                      220

Phe  Arg  Ala  Lys  Ile  Pro  Gly  Leu  Leu  Asn  Gln  Thr  Ser  Arg  Ser  Leu
225                           230                 235                      240

Asp  Gln  Ile  Pro  Gly  Tyr  Leu  Asn  Arg  Ile  His  Glu  Leu  Leu  Asn  Gly
                    245                      250                           255

Thr  Arg  Gly  Leu  Phe  Pro  Gly  Pro  Ser  Arg  Arg  Thr  Leu  Gly  Ala  Pro
               260                      265                      270

Asp  Ile  Ser  Ser  Gly  Thr  Ser  Asp  Thr  Gly  Ser  Leu  Pro  Pro  Asn  Leu
          275                      280                      285

Gln  Pro  Gly  Tyr  Ser  Pro  Ser  Pro  Thr  His  Pro  Pro  Thr  Gly  Gln  Tyr
     290                      295                      300

Thr  Leu  Phe  Pro  Leu  Pro  Pro  Thr  Leu  Pro  Thr  Pro  Val  Val  Gln  Leu
305                      310                      315                      320

His  Pro  Leu  Leu  Pro  Asp  Pro  Ser  Ala  Pro  Thr  Pro  Thr  Pro  Thr  Ser
                    325                      330                      335

Pro  Leu  Leu  Asn  Thr  Ser  Tyr  Thr  His  Ser  Gln  Asn  Leu  Ser  Gln  Glu
               340                      345                      350

Gly
```

( 2 ) INFORMATION FOR SEQ ID NO:5:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( i x ) FEATURE:

(A) NAME/KEY: Modified-site
(B) LOCATION: 29
(D) OTHER INFORMATION: /note= "This amino acid can be any amino acid."

(ix) FEATURE:
(A) NAME/KEY: Modified-site
(B) LOCATION: 31
(D) OTHER INFORMATION: /note= "This amino acid can be any amino acid."

(ix) FEATURE:
(A) NAME/KEY: Modified-site
(B) LOCATION: 33
(D) OTHER INFORMATION: /note= "This amino acid can be any amino acid."

(ix) FEATURE:
(A) NAME/KEY: Modified-site
(B) LOCATION: 34
(D) OTHER INFORMATION: /note= "This amino acid can be Ala, Arg or Lys."

(xi) SEQUENCE DESCRIPTION: SEQ ID NO:5:

| Met | Asp | Ala | Met | Lys | Arg | Gly | Leu | Cys | Cys | Val | Leu | Leu | Leu | Cys | Gly |
|---|---|---|---|---|---|---|---|---|---|---|---|---|---|---|---|
| 1 |  |  |  | 5 |  |  |  |  | 10 |  |  |  |  | 15 |  |

| Ala | Val | Phe | Val | Ser | Pro | Ser | Gln | Glu | Ile | His | Ala | Xaa | Phe | Xaa | Arg |
|---|---|---|---|---|---|---|---|---|---|---|---|---|---|---|---|
|  |  |  | 20 |  |  |  |  | 25 |  |  |  |  | 30 |  |  |

| Xaa | Xaa | Arg |
|---|---|---|
|  |  | 35 |

(2) INFORMATION FOR SEQ ID NO:6:

(i) SEQUENCE CHARACTERISTICS:
(A) LENGTH: 36 base pairs
(B) TYPE: nucleic acid
(C) STRANDEDNESS: single
(D) TOPOLOGY: linear (vii) IMMEDIATE SOURCE:
(B) CLONE: ZC7367

(xi) SEQUENCE DESCRIPTION: SEQ ID NO:6:

CGTCACCGGG AATTCATCGA TATCTAGATA TTAAGA                36

(2) INFORMATION FOR SEQ ID NO:7:

(i) SEQUENCE CHARACTERISTICS:
(A) LENGTH: 43 base pairs
(B) TYPE: nucleic acid
(C) STRANDEDNESS: single
(D) TOPOLOGY: linear (vii) IMMEDIATE SOURCE:
(B) CLONE: ZC7738

(xi) SEQUENCE DESCRIPTION: SEQ ID NO:7:

GCCTTCAGAT CTGCGTCCTC TTCTGAACTC GGCATGATTA AGA        43

(2) INFORMATION FOR SEQ ID NO:8:

(i) SEQUENCE CHARACTERISTICS:
(A) LENGTH: 43 base pairs
(B) TYPE: nucleic acid
(C) STRANDEDNESS: single
(D) TOPOLOGY: linear (vii) IMMEDIATE SOURCE:
(B) CLONE: ZC7365

(xi) SEQUENCE DESCRIPTION: SEQ ID NO:8:

```
GCAAGACTAA CTCTGAGATC TCCCGTAGCT CCTGCCATTA AGA                43
```

(2) INFORMATION FOR SEQ ID NO:9:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (vii) IMMEDIATE SOURCE:
        (B) CLONE: ZC7645

(xi) SEQUENCE DESCRIPTION: SEQ ID NO:9:

```
TGTAGAGGAA GCTGGGTTCC TAGGAGGCCC ATTAAGA                       37
```

(2) INFORMATION FOR SEQ ID NO:10:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (vii) IMMEDIATE SOURCE:
        (B) CLONE: ZC7907

(xi) SEQUENCE DESCRIPTION: SEQ ID NO:10:

```
GCAAGGCTAA CGCTGAGATC TCCGGCTCCT CCTGCTATTA AGA                43
```

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (vii) IMMEDIATE SOURCE:
        (B) CLONE: ZC7693

(xi) SEQUENCE DESCRIPTION: SEQ ID NO:11:

```
GGATCCTTGT GAGCTGTGGT CATTAAGA                                 28
```

(2) INFORMATION FOR SEQ ID NO:12:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (vii) IMMEDIATE SOURCE:
        (B) CLONE: ZC7910

(xi) SEQUENCE DESCRIPTION: SEQ ID NO:12:

```
GATTTGGTCC AGGAATTCCT ACTATTGGTT CAGCAGACCA TTAAGA             46
```

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (vii) IMMEDIATE SOURCE:
        (B) CLONE: ZC7878

(xi) SEQUENCE DESCRIPTION: SEQ ID NO:13:

```
CCGTCTCCTC CTTGGGGCCC ATTAAGA                                                    27
```

( 2 ) INFORMATION FOR SEQ ID NO:14:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC8045

( x i ) SEQUENCE DESCRIPTION: SEQ ID NO:14:

```
AGAAGTCCTG TTTGAATTCT AGTTCAGTGT GAGGACATTA AGA                                  43
```

( 2 ) INFORMATION FOR SEQ ID NO:15:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC7956

( x i ) SEQUENCE DESCRIPTION: SEQ ID NO:15:

```
GCCTTCAGAT CTGCGTCCTC TTTGGAACTC GGCATGATTA AGA                                  43
```